United States Patent [19]

Takeuchi

[11] Patent Number: 5,596,054
[45] Date of Patent: Jan. 21, 1997

[54] TRANSITION METAL COMPOUND, POLYMERIZATION CATALYST USING SAME AND PROCESS FOR PRODUCING STYRENIC POLYMER USING SAID POLYMERIZATION CATALYST

[75] Inventor: Mizutomo Takeuchi, Ichihara, Japan

[73] Assignee: Idemitsu Kosan Co., Ltd., Tokyo, Japan

[21] Appl. No.: 401,982

[22] Filed: Mar. 10, 1995

[30] Foreign Application Priority Data

Mar. 11, 1994 [JP] Japan .................................. 6-041315

[51] Int. Cl.$^6$ .............................. C08F 4/69; C08F 4/643; C08F 12/08
[52] U.S. Cl. .................. 526/134; 526/114; 526/115; 526/126; 526/127; 526/132; 526/133; 526/160; 526/170; 526/285; 526/347.2; 526/943; 526/52; 502/103; 502/118; 502/123; 502/124; 502/152; 502/155; 502/202
[58] Field of Search .................. 556/11, 43, 52, 556/58, 285; 526/126, 127, 160, 170, 171, 285, 114, 115, 132, 133, 134, 943, 347.2; 502/103, 118, 123, 124, 155, 202, 152

[56] References Cited

U.S. PATENT DOCUMENTS 3,306,919  2/1967  Brantley et al. .................. 526/160 X
5,066,741  11/1991 Campbell, Jr. .................... 526/160 X
5,399,635  3/1995  Neithamer et al. ............... 526/348.2 X

FOREIGN PATENT DOCUMENTS 0322663  7/1989  European Pat. Off. .
0421659  4/1991  European Pat. Off. .

*Primary Examiner*—Fred Teskin
*Attorney, Agent, or Firm*—Oblon, Spivak, McClelland, Maier & Neustadt, P.C.

[57] ABSTRACT

There are disclosed a transition metal compound of the general formula $RMX_{a-1}L_b$ (R is as a π ligand, a fused polycyclic cyclopentadienyl group in which at least one of many-membered rings to which cyclopentadienyl groups are fusedly bonded is a saturated ring, M is a transition metal, X is a σ ligand, L is a Lewis base, a is the valency of M, and b is 0, 1 or 2); a polymerization catalyst for styrene, etc. comprising the above transition metal, preferably further comprising an oxygen atom containing compound ionic compound or organoboron compound and optionally a Lewis base; and a process for producing a polymer of a compound containing an ethylenically unsaturated double bond or an acetylenic polymer, especially a syndiotactic polystyrene by using the above polymerization catalyst. The catalyst is particularly effectivive for producing highly syndiotactic polystyrene minimized in residual metals amounts at a low cost in enhanced efficiency.

18 Claims, No Drawings

5,596,054

TRANSITION METAL COMPOUND, POLYMERIZATION CATALYST USING SAME AND PROCESS FOR PRODUCING STYRENIC POLYMER USING SAID POLYMERIZATION CATALYST

BACKGROUND OF THE INVENTION

1. Field of the Invention

The present invention relates to a transition metal compound, a polymerization catalyst using the same and a process for producing a styrenic polymer using said catalyst. More particularly, it pertains to a transition metal compound which is useful as a component of a polymerization catalyst for a compound containing an ethylenically unsaturated double bond or acetylene series, especially of a polymerization catalyst for styrene series; a highly active polymerization catalyst which contains the above-mentioned transition metal compound and serves for a compound containing an ethylenically unsaturated double bond or acetylene series; and a process for efficiently producing at a low cost, a styrenic polymer which has a high degree of syndiotactic configuration and is minimized in the amounts of residual metals by the use of the aforesaid polymerization catalyst.

2. Description of Related Arts

Olefinic polymers such as polyethylene and polypropylene find their great use as a general-purpose resin in a variety of fields. It is known that the aforesaid olefinic polymers are produced in the presence of a catalytic system containing Ziegler-Natta catalyst as a principal catalytic component. Recently an attempt is made to produce an olefinic polymer by the use of a polymerization catalyst comprising as a catalytic component, a transition metal compound having a π ligand in which said π ligand is bonded to a central metallic element through an arbitrary group.

For example, there are disclosed catalysts for olefins polymerization comprising as a catalytic component, a transition metal compound having a π ligand in which said π ligand is bonded to a central metallic element through an arbitrary group as well as processes for producing olefinic polymers by the use of the catalysts in European Patent Application Laid-Open Nos. 420436, 418044, 416815, 468651, 495375, 514828 and 520732, International Publication No. 00333/1992, etc.

However, sufficiently satisfactory catalytic-activity has not been obtained from a catalyst among them comprising a transition metal compound in which the π ligand is a fused polycyclic cyclopentadienyl group containing an aromatic ring such as indenyl group or fluorenyl group.

Heretofore, styrenic polymers produced by the radical polymerization method or the like have an atactic configuration in stereostructure and are molded to various shapes by various molding methods such as injection molding, extrusion molding, blow molding, vacuum molding and cast molding, and they have been widely used as domestic electrical appliances, office machines, household goods, packaging containers, toys, furnitures, synthetic papers, sheets, films and other industrial materials.

However, such styrenic polymers having atactic configuration have disadvantage that it is inferior in heat resistance and chemical resistance. On the other hand, since the styrene polymers having a syndiotactic configuration have melting points which are different from those of the conventional atactic polystyrenes, and are higher than those of the isotactic polystyrenes known so far, they are expected to be used as heat-resistant resins in various fields.

The group to which the present inventors belong has previously found that the use of a combined catalyst of an aluminoxane with a transition metal compound having an indenyl group as a π ligand can produce a styrenic polymer having a syndiotactic configuration (refer to Japanese Patent Application Laid-Open No. 294705/1989). However, the catalyst comprising the transition metal compound containing, as a π ligand, a fused polycyclic cyclopentadienyl group having an aromatic ring such as an indenyl group suffers a disadvantage that the catalyst fails to attain a sufficient catalytic activity.

SUMMARY OF THE INVENTION

Under such circumstances, it is an object of the present invention to provide a novel transition metal compound which is useful as a component of a polymerization catalyst for a compound containing an ethylenically unsaturated double bond or acetylene series, especially of a polymerization catalyst for styrene series.

It is another object of the present invention to provide a highly active polymerization catalyst which comprises the above-mentioned transition metal compound and serves for a compound containing an ethylenically unsaturated double bond or acetylene series.

It is a further object of the present invention to provide a process for efficiently producing at a low cost, a styrenic polymer which has a high degree of syndiotactic configuration and is minimized in the amounts of residual metals by the use of the aforesaid polymerization catalyst.

In order to achieve the above-mentioned objects, intensive research and investigation were continued by the present inventors. As a result, it has been found that a transition metal compound of a specific constitution having, as a π ligand, a fused polycyclic cyclopentadienyl group in which at least one of many-membered rings to which cyclopentadienyl groups are fusedly bonded is a saturated ring is useful as a component of a polymerization catalyst for a compound containing an ethylenically unsaturated double bond or acetylene series; that a polymerization catalyst which comprises in combination, the above-mentioned transition metal, at least one from an oxygen atom containing compound, a specified ionic compound and an organoboron compound and optionally a Lewis acid possesses a high activity and thereby can efficiently polymerize a compound containing an ethylenically unsaturated double bond or acetylene series; and in particular that a styrenic polymer which has a high degree of syndiotactic configuration and is minimized in the amounts of residual metals is efficiently obtained at a low cost by polymerizing a styrenic polymer using the aforesaid polymerization catalyst. The present invention has been accomplished on the basis of the aforestated finding and information.

Specifically, the present invention provides a transition metal compound which is characteristically represented by the general formula (I)

$$RMX_{a-1}L_b \qquad (I)$$

wherein R is, as a π ligand, a fused polycyclic cyclopentadienyl group wherein at least one of many-membered rings to which cyclopentadienyl groups are fusedly bonded is a saturated ring, M is a transition metal, X is a σ ligand, a plurality of X may be the same or different and bonded to each other through an arbitrary group, L is a Lewis base, a is the valency of M, b is 0, 1 or 2 and when L is plural, each L may be the same or different; a polymerization catalyst for a compound containing an ethylenically unsaturated double bond or acetylene series which catalyst comprises the above-mentioned transition metal compound; and a particularly preferable polymerization catalyst for a compound containing an ethylenically unsaturated double bond or acetylene series which catalyst comprises in combination the above-mentioned (A) transition metal compound; (B) at least one member selected from the group consisting of an (1) oxygen atom containing compound, an (2) ionic compound comprising a noncoordinate anion and a cation and an (3) organoboron compound; and optionally a (C) Lewis acid.

Furthermore, the present invention provides a process for producing a styrenic polymer which comprises polymerizing a styrenic monomer or a styrenic monomer along with an other polymerizable unsaturated compound in the presence of any of the aforesaid polymerization catalyst and moreover, a process for producing a polymer of a compound containing an ethylenically unsaturated double bond or an acetylenic polymer by using the aforesaid polymerization catalyst.

DESCRIPTION OF PREFERRED EMBODIMENTS

The transition metal compound according to the present invention has the constitution represented by the general formula (I)

wherein R is, as a π ligand, a fused polycyclic cyclopentadienyl group in which at least one of many-membered rings to which cyclopentadienyl groups are fusedly bonded is a saturated ring. The above-mentioned fused polycyclic cyclopentadienyl group is exemplified by that selected from those represented by any one of the general formulae (II) to (IV)

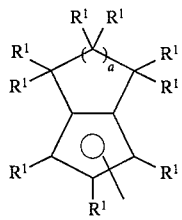

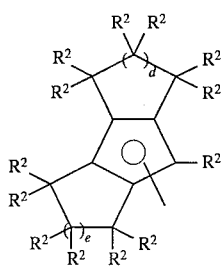

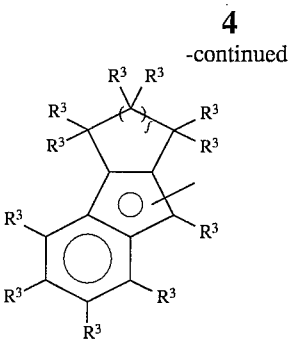

wherein $R^1$, $R^2$ and $R^3$ are each a hydrogen atom, a halogen atom, an aliphatic hydrocarbon group having 1 to 20 carbon atoms, an aromatic hydrocarbon group having 6 to 20 carbon atoms, an alkoxyl group having 1 to 20 carbon atoms, an aryloxyl group having 6 to 20 carbon atoms, a thioalkoxyl group having 1 to 20 carbon atoms, a thioaryloxyl group having 6 to 20 carbon atoms, an amino group, an amide group, a carboxyl group or an alkylsilyl group and may be the same as or different from each other; and c, d, e and f are each an integer of 1 or greater. Of these, 4,5,6,7-tetrahydroindenyl group is preferable from the viewpoint of catalytic activity and the ease of its synthesis.

Specific examples of R include 4,5,6,7-tetrahydroindenyl group; 1-methyl-4,5,6,7-tetrahydroindenyl group; 2-methyl-4,5,6,7-tetrahydroindenyl group; 1,2-dimethyl-4,5,6,7-tetrahydroindenyl group; 1,3-dimethyl-4,5,6,7-tetrahydroindenyl group; 1,2,3-trimethyl-4,5,6,7-tetrahydroindenyl group; 1,2,3,4,5,6,7-heptamethyl-4,5,6,7-tetrahydroindenyl group; 1,2,4,5,6,7-hexamethyl-4,5,6,7-tetrahydroindenyl group; 1,3,4,5,6,7-hexamethyl-4,5,6,7-tetrahydroindenyl group; octahydrofluorenyl group; 1,2,3,4-tetrahydrofluorenyl group; 9-methyl-1,2,3,4-tetrahydrofluorenyl group; and 9-methyl-octahydrofluorenyl group.

M is a transition metal and exemplified by titanium, zirconium, hafnium, lanthanoids, niobium and tantalum. Of these titanium is preferable from the viewpoint of catalytic activity. X is a σ ligand and is exemplified by a hydrogen atom, a halogen atom, an aliphatic hydrocarbon group having 1 to 20 carbon atoms, an aromatic hydrocarbon group having 6 to 20 carbon atoms, an alkoxyl group having 1 to 20 carbon atoms, an aryloxyl group having 6 to 20 carbon atoms, a thioalkoxyl group having 1 to 20 carbon atoms, a thioaryloxyl group having 6 to 20 carbon atoms, an amino group, an amide group, a carboxyl group or an alkylsilyl group, and a plurality of X may be the same or different and bonded to each other through an arbitrary group. Further, X is specifically exemplified by hydrogen atom, chlorine atom, bromine atom, iodine atm, methyl group, benzyl group, phenyl group, trimethylsilylmethyl group, methoxy group, ethoxy group, phenoxy group, thiomethoxy group, thiophenoxy group, dimethylamino group and diisopropylamino group. L is a Lewis base, a is the valency of M and b is 0, 1 or 2.

As the transition metal compound represented by the general formula (I), there can preferably be employed a compound comprising R and X each arbitrarily selected from the above-exemplified groups.

The transition metal compound represented by the general formula (I) is specifically exemplified by but not limited to 4,5,6,7-tetrahydroindenyltitanium trichloride; 4,5,6,7-tetrahydroindenyltrimethyltitanium; 4,5,6,7-tetrahydroindenyltribenzyltitanium; 4,5,6,7-tetrahydroindenyltitanium trimethoxide; 1-methyl-4,5,6,7-tetrahydroindenyltitanium trichloride; 1-methyl-4,5,6,7-tetrahydroindenyltrimethyltitanium; 1-methyl-4,5,6,7-tetrahydroindenyltribenzyltitanium; 1-methyl-4,5,6,7-tetrahydroindenyltitanium trimethoxide; 2-methyl-4,5,6,7-tetrahydroindenyltitanium trichloride; 2-methyl-4,5,6,7-tetrahydroindenyltrimethyltitanium; 2-methyl-4,5,6,7-tetrahydroindenyltribenzyltitanium; 2-methyl-4,5,6,7-tetrahydroindenyltitanium trimethoxide; 1,2-dimethyl-4,5,6,7-tetrahydroindenyltitanium trichloride; 1,2-dimethyl-4,5,6,7-tetrahydroindenyltrimethyltitanium; 1,2-dimethyl-4,5,6,7-tetrahydroindenyltribenzyltitanium; 1,2-dimethyl-4,5,6,7-tetrahydroindenyltitanium trimethoxide; 1,3-dimethyl-4,5,6,7-tetrahydroindenyltitanium trichloride; 1,3-dimethyl-4,5,6,7-tetrahydroindenyltrimethyltitanium; 1,3-dimethyl-4,5,6,7-tetrahydroindenyltribenzyltitanium; 1,3-dimethyl-4,5,6,7-tetrahydroindenyltitanium trimethoxide; 1,2,3-trimethyl-4,5,6,7-tetrahydroindenyltitanium trichloride; 1,2,3-trimethyl-4,5,6,7-tetrahydroindenyltrimethyltitanium; 1,2,3-trimethyl-4,5,6,7-tetrahydroindenyltribenzyltitanium; 1,2,3-trimethyl-4,5,6,7-tetrahydroindenyltitanium trimethoxide; 1,2,3,4,5,6,7-heptamethyl-4,5,6,7-tetrahydroindenyltitanium trichloride; 1,2,3,4,5,6,7-heptamethyl-4,5,6,7-tetrahydroindenyltrimethyltitanium; 1,2,3,4,5,6,7-heptamethyl-4,5,6,7-tetrahydroindenyltribenzyltitanium;1,2,3,4,5,6,7-heptamethyl-4,5,6,7-tetrahydroindenyltitanium trimethoxide; 1,2,4,5,6,7-hexamethyl-4,5,6,7-tetrahydroindenyltitanium trichloride; 1,2,4,5,6,7-hexamethyl-4,5,6,7-tetrahydroindenyltrimethyltitanium; 1,2,4,5,6,7-hexamethyl-4,5,6,7-tetrahydroindenyltribenzyltitanium; 1,2,4,5,6,7-hexamethyl-4,5,6,7-tetrahydroindenyltitanium trimethoxide; 1,3,4,5,6,7-hexamethyl-4,5,6,7-tetrahydroindenyltitanium trichloride; 1,3,4,5,6,7-hexamethyl-4,5,6,7-tetrahydroindenyltrimethyltitanium; 1,3,4,5,6,7-hexamethyl-4,5,6,7-tetrahydroindenyltribenzyltitanium; 1,3,4,5,6,7-hexamethyl-4,5,6,7-tetrahydroindenyltitanium trimethoxide; octahydrofluorenyltitanium trichloride; octahydrofluorenyltrimethyltitanium; octahydrofluorenyltribenzyltitanium; octahydrofluorenyltitanium trimethoxide; 1,2,3,4-tetrahydrofluorenyltitanium trichloride;1,2,3,4-tetrahydrofluorenyltrimethyltitanium; 1,2,3,4-tetrahydrofluorenyltribenzyltitanium; 1,2,3,4-tetrahydrofluorenyltitanium trimethoxide; 9-methyl-1,2,3,4-tetrahydrofluorenyltitanium trichloride; 9-methyl-1,2,3,4-tetrahydrofluorenyltrimethyltitanium; 9-methyl-1,2,3,4-tetrahydrofluorenyltribenzyltitanium; 9-methyl-1,2,3,4-tetrahydrofluorenyltitanium trimethoxide; 9-methyl octahydrofluorenyltitanium trichloride; 9-methyloctahydrofluorenyltrimethyltitanium; 9-methyloctahydrofluorenyltribenzyltitanium; 9-methyloctahydrofluorenyltitanium trimethoxide; any of the above-mentioned compounds in which the titanium is replaced with zirconium or hafnium and a similar compound in which the transition metal element belongs to an other series or lanthanoids. Of these the titanium compounds are preferable from the viewpoint of catalytic activity.

The polymerization catalyst for a compound containing an ethylenically unsaturated double bond or acetylene series according to the present invention comprises the transition metal compound represented by the general formula (I). In particular, the preferable catalysts are a polymerization catalyst which comprises in combination the (A) transition metal compound as previously defined; and (B) at least one member selected from the group consisting of an (1) oxygen atom containing compound, an (2) ionic compound comprising a noncoordinate anion and a cation and an (3) organoboron compound; and a polymerization catalyst which comprises in combination the (A) transition metal compound as previously defined; (B) at least one member selected from the group consisting of an (1) oxygen atom containing compound, an (2) ionic compound comprising a noncoordinate anion and a cation and an (3) organoboron compound; and a (C) Lewis acid because of their excellent catalytic activity.

As the oxygen atom-containing compound as the component (b), there are used such compound having a chain structure represented by the general formula (I')

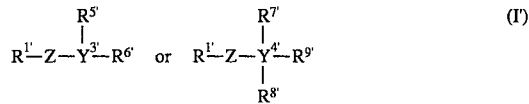

and/or such compound having a cyclic structure represented by the general formula (II')

In the above-mentioned general formulae (I') and (II'), Z is a structure in which one or more groups represented by the formula

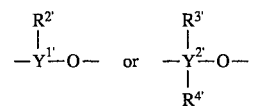

are arranged in an arbitrary order in the number of arbitrary positive integers; $R^{1'}$ to $R^{9'}$ are each an alkyl group having 1 to 8 carbon atoms and specifically exemplified by methyl group, ethyl group, n-propyl group, isopropyl group, various butyl groups, various pentyl groups, various hexyl groups, various heptyl groups and various octyl groups; $R^{1'}$ to $R^{9'}$ may be the same as or different from each other; $Y^{1'}$ and $Y^{3'}$ are each a Group 13 metal of the Periodic Table and specifically exemplified by B, Al, Ga, In and Tl, among which B and Al are preferable; $Y^{1'}$ and $Y^{3'}$ may be the same as or different from each other; $Y^{2'}$ and $Y^{4'}$ are each a Group 14 metal of the Periodic Table and specifically exemplified by C, Si, Ge, Sn and Pb, among which C and Si are preferable; $Y^{2'}$ to $Y^{4'}$ may be the same as or different from each other;

As the oxygen atom-containing compound represented by the general formula (I') or (II'), there is preferably usable the reaction product between an organoaluminum compound and water, which product is principally a chain alkylaluminoxane represented by the general formula (XII)

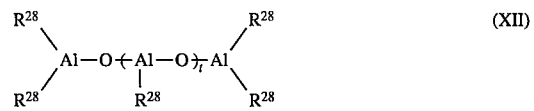

wherein t is a number from 2 to 50 indicating polymerization degree and $R^{28}$ represents an alkyl group having 1 to 8 carbon atoms, a cycloalkylaluminoxane having the repeating unit represented by the general formula (XIII):

wherein $R^{28}$ is as previously defined and the like. Of these alkylaluminoxanes, that wherein $R^{28}$ is a methyl group, i.e. methylaluminoxane is particularly preferred.

As the organoaluminum compound to be reacted with water, mention is made of an organoaluminum compound represented by the general formula (XIV)

wherein $R^{28}$ is as previously defined, more specifically, trimethylaluminum, triethylaluminum, triisobutylaluminum and the like and among them trimethylaluminum is particularly desirable.

Generally, the reaction product of an alkylaluminum compound such as trialkylaluminum with water contains the above-mentioned chain alkylaluminoxane and cycloalkylaluminoxane as principal components, unreacted trialkylaluminum, a mixture of various condensation products, and further complicatedly associated molecules thereof, which becomes various products according to the contacting conditions of the trialkylaluminum compound and water.

The reaction of the trialkylaluminum compound with water is not specifically limited, but can be performed according to any of known methods.

The oxygen atom-containing compound as the component (b) in the present invention may be used alone or in combination with at least one other one. Also there may be used as the component (B) at least one compound of the component (a) in combination with at least one compound of the component (b).

Examples of the ionic compound comprising a noncoordinate anion and a cation as the component (2) in the component (B) include a compound represented by the general formula (VII) or (VIII)

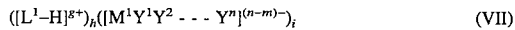  (VII)

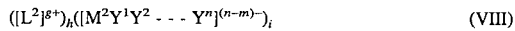  (VIII)

wherein $L^2$ is $M^3$, $R^5R^6M^4$ or $R^7{}_3C$ as hereinafter described; $L^1$ is a Lewis base; $M^1$ and $M^2$ are each an element selected from Groups 5 to 15 of the Periodic Table and exemplified by B, Al, P, As and Sb; $M^3$ is an element selected from Groups 8 to 12 of the Periodic Table and exemplified by Ag and Cu; $M^4$ is an element selected from Groups 8 to 10 of the Periodic Table and exemplified by Fe, Co and Ni; $Y^1$ to $Y^n$ are each a hydrogen atom, dialkylamino group, alkoxy group, aryloxy group, alkyl group having 1 to 20 carbon atoms, aryl group having 6 to 20 carbon atoms, arylalkyl group, alkylaryl group, substituted alkyl group, organometalloid group or halogen atom and exemplified by dimethylamino group, diethylamino group, methoxy group, ethoxy group, butoxy group, phenoxy group, 2,6-dimethylphenoxy group, methyl group, ethyl group, propyl group, butyl group, octyl group, phenyl group, tolyl group, xylyl group, mesityl group, benzyl group, pentafluorophenyl group, 3,5-di(trifluoromethyl)group, 4-tert-butylphenyl group, F, Cl, Br, I, pentamethylantimony group, trimethylsilyl group, trimethylgermyl group and diphenylboron group; $R^5$ and $R^6$ are each a cyclopentadienyl group, substituted cyclopentadienyl group, indenyl group, substituted indenyl group or fluorenyl group and exemplified by methylcyclopentadienyl group and pentamethylcyclopentadienyl group; $R^7$ is an alkyl group, aryl group or a substituted aryl group, may be the same or different and exemplified by a phenyl group, 4-methoxyphenyl group and 4-methylphenyl group; m is the valency of each of $M^1$ and $M^2$, indicating an integer from 1 to 7; n is an integer from 2 to 8; g is the ion valency of each of [$L^1$–H] and [$L^2$], indicating an integer from 1 to 7; h is an integer of 1 or greater and $i=(h \times g)/(n-m)$.

Examples of the noncoordinate anion in the aforestated ionic compound include (tetraphenyl)borate; tetra(fluorophenyl)borate; tetrakis(difluorophenyl)borate; tetrakis(trifluorophenyl)borate; tetrakis(tetrafluorophenyl)borate; tetrakis(pentafluorophenyl)borate; tetrakis(trifluoromethylphenyl)borate; tetra(tolyl)borate; tetra(xylyl)borate; (triphenylpentafluorophenyl)borate; [tris(pentafluorophenyl)phenyl]borate and tridecahydride-7,8-dicarbaundecaborate.

Examples of the cation in the above-mentioned ionic compound include triethyl ammonium; tributyl ammonium; N,N'-dimethylanilinium; N,N'-diethylanilinium; triphenylphosphinium; dimethylphenylphosphinium; 1,1'-dimethylferrocene; decamethylferrocene; silver (I); triphenylcarbenium; tritolylcarbenium; trimethoxyphenylcarbenium; (ditolylphenyl)carbenium; [di(methoxyphenyl)phenyl]carbenium and [methoxyphenyl di(phenyl)]carbenium.

The above-mentioned ionic compound can preferably be used by optionally selecting the noncoordinate anion and cation from among the above-exemplified examples and combining the selected ones.

Among the compounds represented by the general formula (VII) or (VIII), specific examples of preferably usable compounds include, as the compound of general formula (VII), triethylammonium tetraphenylborate, tri(n-butyl) ammonium tetraphenylborate, trimethylammonium tetraphenylborate, triethylammonium tetrakis(pentafluorophenyl)borate, tri(n-butyl)ammonium tetrakis(pentafluorophenyl)borate, triethylammonium hexafluoroarsenate, etc., and as the compound of general formula (VIII), pyridinium tetrakis(pentafluorophenyl)borate, pyrrolinium tetrakis(pentafluorophenyl)borate, N,N-dimethylanilinium tetrakis(pentafluorophenyl)borate, methyldiphenylammonium tetrakis(pentafluorophenyl)borate, ferrocenium tetraphenylborate, dimethylferrocenium tetrakis(pentafluorophenyl)borate, ferrocenium tetrakis(pentafluorophenyl)borate, decamethylferrocenium tetrakis(pentafluorophenyl)borate, acetylferrocenium tetrakis(pentafluorophenyl)borate, formylferrocenium tetrakis(pentafluorophenyl)borate, cyanoferrocenium tetrakis(pentafluorophenyl)borate, silver tetraphenylborate, silver tetrakis(pentafluorophenyl)borate, trityl tetraphenylborate, trityl tetrakis(pentafluorophenyl)borate, silver hexafluoroarsenate, silver hexafluoroantimonate, silver tetrafluoroborate, etc.

Examples of the organoboron compounds usable as the component (3) include the compound represented by the general formula (IX)

  (IX)

wherein $R^8$ is an aliphatic hydrocarbon group having 1 to 20 carbon atoms, an aromatic hydrocarbon group having 6 to 20 carbon atoms, a substituted aromatic hydrocarbon group, hydrogen atom or a halogen atom, may be the same or different and specifically exemplified by a phenyl group, tolyl group, fluorophenyl group, trifluoromethylphenyl group, pentafluorophenyl group, fluorine atom, chlorine atom, bromine atom and iodine atom; $L^3$ is a Lewis base and exemplified by an ether compound such as diethyl ether and tetrahydrofuran and an amine compound such as pyridine; and v is an integer from 0 to 3. Specific examples thereof include trisphenylboron, tris(pentafluorophenyl)boron, triethylboron, di(pentafluorophenyl)phenylboron and tris(3,5-ditrifluoromethylphenyl)boron.

As the aforesaid component (B) in the polymerization catalyst according to the present invention, the aluminoxane as the component (1) may be used alone or in combination with at least other one, the ionic compound as the component (2) may be used alone or in combination with at least other one, the organoboron compound as the component (3) may be used alone or in combination with at least other one, and in addition, the components (1), (2) and (3) may be used in optional combination with each other.

Examples of the Lewis acid as the component (C) to be used when desired in the polymerization catalyst according to the present invention include an organoaluminum compound, a magnesium compound, zinc compound and lithium compound.

Specific examples of the above-mentioned organoaluminum compound include the compound represented by the general formula (X)

$$R^9{}_r Al(OR^{10})_s H_t Z_u \quad (X)$$

wherein $R^9$ and $R^{10}$ independently of one another, are each an alkyl group having 1 to 8 carbon atoms and may be the same or different; Z is an halogen atom; r, s, t and u each satisfy the relations $0<r\leq 3$, $0<s\leq 3$, $0\leq t<3$ and $0\leq u<3$ and $r+s+t+u=3$.

In the organoaluminum compound represented by the general formula (IX), the compound wherein s=t=u=0 and r=3 is exemplified by trimethylaluminum, triethylaluminum, triisopropylaluminum, triisobutylaluminum and trioctylaluminum. In the case of t=u=0 and $1.5<r\leq 3$, the compound is exemplified by diethylaluminum ethoxide, dibutylaluminum butoxide, diethylaluminum sesquiethoxide and dibutylaluminum sesquibutoxide; as well as partially alkoxylated alkylaluminum.

Examples of the compound corresponding to the case where s=t=0 include diethylaluminum dichloride and dibutylaluminum dichloride (r=2); ethylaluminum sesquichloride and butylaluminum sesquichloride (r=1.5); and ethylaluminum dichloride and butylaluminum dichloride (r=1).

Examples of the compound corresponding to the case in which s=u=0 include diethylaluminum hydride and diisobutylaluminum hydride (r=2); and ethylaluminum dihydride and butylaluminum dihydride (r=1).

Examples of the above-mentioned magnesium compound include a Grignard compound such as methylmagnesium bromide, ethylmagnesium bromide, phenylmagnesium bromide and benzylmagnesium bromide, an organomagnesium compound such as diethoxymagnesium and ethylbutylmagnesium and an inorganic magnesium compound such as magnesium chloride. In addition, mention may be made of a zinc compound exemplified by an organozinc compound such as diethylzinc and of a lithium compound exemplified by an organolithium compound such as methyllithium.

As a method for contact-mixing the components (A) and (B) and the component (C) to be used when desired, mention may be made of ① a method in which the component (C) is added to the contact mixture between the components (A) and (B) to form a catalyst, which is brought into contact with a monomer component to be polymerized; ② a method in which the component (A) is added to the contact mixture between the components (B) and (C) to form a catalyst, which is brought into contact with a monomer component to be polymerized; ③ a method in which the component (B) is added to the contact mixture between the components (A) and (C) to form a catalyst, which is brought into contact with a monomer component to be polymerized; ④ a method in which the components (A), (B) and (C) are each separately brought into contact with a monomer component to be polymerized; and ⑤ a method in which the catalyst prepared in the above-mentioned ①, ② or ③ is brought into contact with the contact mixture between the monomer component to be polymerized and the component (C).

The contact mixing among the components (A) and (B) and the component (C) to be used as desired can be carried out at a temperature in the range of −20° to 200° C., needless to say, at a polymerization temperature.

The polymerization catalyst comprising in combination the components (A) and (B) or the components (A), (B) and (C) may be further incorporated with an other catalyst component.

The blending ratio of the catalyst components varies depending upon various conditions and thus can not unequivocally be determined. However, when the component (B) is aluminoxane, the molar ratio of the component (A) to the component (B) is selected so as to be 1:1 to 1:10,000, preferably 1:1 to 1:1,000. In the case where the component (B) is an ionic compound comprising a noncoordinate anion and a cation, or an organoboron compound, the molar ratio of the component (A) to the component (B) is preferably selected so as to be 0.1:1 to 1:0.1. The molar ratio of the component (A) to the component (C) when used, is selected so as to be 1:0.1 to 1:1,000.

The polymerization catalyst according to the present invention is used for the polymerization of acetylene series or a compound containing an ethylenically unsaturated double bond, which is exemplified by an olefin, a diolefin compound and styrene series.

Examples of such olefin include α-olefins such as ethylene; propylene; butene-1; pentene-1; hexene-1; heptene 1; octene-1; nonene-1; decene-1; 4-phenylbutene-1; 6-phenylhexene-1; 3-methylbutene-1; 4-methylpentene-1; 3-methylpentene-1; 3-methylhexene-1; 4-methylhexene-1; 5-methylhexene-1; 3,3-dimethylpentene-1; 3,4-dimethylpentene-1; 4,4-dimethylpentene-1; and vinylcyclohexane, halogen-substituted α-olefins such as hexafluoropropene; tetrafluoroethylene; 2-fluoropropene; fluoroethylene; 1,1difluoroethylene; 3-fluoropropene; trifluoroethylene; and 3,4-dichlorobutene-1, cyclic olefins such as cyclopentene; cyclohexene; norbornene; 5-methylnorbornene; 5-ethylnorbornene; 5-propylnorbornene; 5,6-dimethylnorbornene; 1-methylnorbornene; 7-methylnorbornene; 5,5,6-trimethylnorbornene; 5-phenylnorbornene; and 5-benzylnorborene.

Examples of the diolefin compound include straight chain diolefins such as butadiene; isoprene; and 1,6-hexadiene, and cyclic diolefins such as norbornadiene; 5-ethylidenenorbornene; 5-vinylnorbornene; 5-vinylcyclohexene;and dicyclopentadiene.

Examples of the styrene series include styrene, alkylstyrenes such as p-methylstyrene; m-methylstyrene; omethylstyrene; 2,4-dimethylstyrene; 2,5-dimethylstyrene; 3,4-dimethylstyrene; 3,5-dimethylstyrene; and p-tertiarybutylstyrene; alkoxystyrenes such as p-methoxystyrene; m-methoxystyrene; and o-methoxystyrene; halogenated styrenes such as p-chlorostyrene; m-chlorostyrene; o-chlorostyrene; p-bromostyrene; m-bromostyrene; o-bromostyrene; p-fluorostyrene; m-fluorostyrene; o-fluorostyrene and o-methyl-p-fluorostyrene; organosiliconated styrenes, vinylbenzoic acid esters and divinylbenzene.

Examples of the acetylene series include acetylene, methylacetylene, phenylacetylene and trimethylsilylacetylene.

The above-mentioned monomer may be polymerized alone or in combination with at least one other monomer.

The polymerization method may be bulk polymerization method without specific limitation. The polymerization may be carried out in an aliphatic hydrocarbon solvent such as pentane, hexane and heptane, an alicyclic hydrocarbon solvent such as cyclohexane or an aromatic hydrocarbon solvent such as benzene, toluene, xylene and ethylbenzene.

The polymerization temperature is not specifically limited but is usually 0° to 200° C., preferably 20° to 100° C. In the case where a gaseous monomer is employed, the partial pressure of the gaseous monomer is usually 300 kg/cm$_2$ (29.4199×10$^6$ Pa) or lower, preferably 30 kg/cm$^2$ (2.94199× 10$^6$ Pa) or lower.

It is preferable in the present invention that the above-mentioned catalyst be employed for the production of a styrenic polymer in particular. In this case, a styrenic monomer may be homopolymerized or copolymerized with at least one other comonomer. In addition, at least one styrenic monomer may be copolymerized with at least one polymerizable unsaturated compound, which is exemplified by olefin, diolefin compound and acetylene series.

The styrenic polymer obtained by the use of the above-mentioned catalyst has a high degree of syndiotactic configuration in its styrenic chain. In this case, a high degree of syndiotactic configuration in the styrenic chain of the styrenic polymer signifies that its stereochemical structure is of high degree of syndiotactic configuration, i,e., the stereostructure in which phenyl groups or substituted phenyl groups as side chains are located alternately at opposite directions relative to the main chain consisting of carbon-carbon bonds. Tacticity is quantitatively determined by the nuclear magnetic resonance method ($^{13}$C-NMR method) using carbon isotope. The tacticity as determined by the $^{13}$C-NMR method can be indicated in terms of proportions of structural units continuously connected to each other, i.e., a diad in which two structural units are connected to each other, a triad in which three structural units are connected to each other and a pentad in which five structural units are connected to each other. "The styrenic polymers having such a high degree of syndiotactic configuration" as mentioned in the present invention usually means polystyrene, poly(substituted styrene), poly(vinyl benzoate), the mixture thereof, and copolymers containing the above polymers as main components, having such a syndiotacticity that the proportion of racemic diad is at least 75%, preferably at least 85%, or the proportion of racemic pentad is at least 30%, preferably at least 50%. The poly(substituted styrene) includes poly(hydrocarbon group-substituted styrene) such as poly(methylstyrene), poly(ethylstyrene), poly(isopropylstyrene), poly(phenylstyrene) and poly(vinylstyrene); poly(halogenated styrene) such as poly(chlorostyrene), poly(bromostyrene), and poly(fluorostyrene); and poly(alkoxystyrene) such as poly(methoxystyrene) and poly(ethoxystyrene). Examples of the particularly preferable styrenic polymers among them include polystyrene, poly(p-methylstyrene), poly(m-methylstyrene), poly(p-tertiary-butylstyrene), poly(p-chlorostyrene), poly(m-chlorostyrene), poly(p-fluorostyrene) and a copolymer of styrene and p-methylstyrene.

By virtue of its specific constitution having, as a ligand, a fused polycyclic cyclopentadienyl group in which at least one of many-membered rings to which cyclopentadienyl groups are fusedly bonded is a saturated bone, the transition metal compound according to the present invention is useful as a component of a polymerization catalyst for a compound containing an ethylenically unsaturated double bond or acetylene series, especially for styrene series.

In addition, the polymerization catalyst comprising the above-mentioned transition metal compound has a high activity and is preferably used for the polymerization of a compound containing an ethylenically unsaturated double bond or acetylene series. In particular, by homopolymerizing or copolymerizing styrene series by the use of the aforesaid polymerization catalyst, there is obtained a styrenic polymer having a high degree of syndiotactic configuration and minimized in the amounts of residual metals at a low cost in high efficiency.

In the following, the present invention will be described in more detail with reference to non-limitative examples.

EXAMPLE1

Synthesis of 1,2,3-trimethyl-4,5,6,7-tetrahydroindenyltitanium trichloride (Compound A)

(1) Synthesis of 2,3-dimethyl-4,5,6,7-tetrahydroinde-1-one

In 500 g of polyphosphoric acid were added 32.9 g (400 mmol) of cyclohexene and 40.3 g of tiglic acid with heating to 60° C. and stirring for 2 hours. After temperature lowering, the resultant reddish yellow viscous solution was added dropwise to 1000 milliliter (hereinafter abbreviated to "mL") of water to form yellow suspension, which was then extracted with 700 mL of ethyl ether, separated and washed with saturated aqueous solution of sodium chloride. Thus, the resultant organic phase was dried with magnesium sulfate. anhydride. After the separation of the drying agent, the solvent was distilled away and the resultant product was distilled under reduced pressure to obtain 39.2 g of the objective product from the fraction at 85° to 87° C. under 3 mm (2) Synthesis of 1,2,3-trimethyl-4,5,6,7-tetrahydroinde-1-ol In 100 mL of dried diethyl ether were added 16.2 g (99.6 mmol) of 2,3-dimethyl-4,5,6,7-tetrahydroinde-1-one as obtained in the foregoing step (1) and further 100 mL of solution of 1.4 M methyllithium in diethyl ether to proceed with reaction at room temperature for one hour, followed by refluxing with heating for 15 hours. After temperature lowering, a small amount of water was added to the reaction system, and the resultant organic phase was separated and dried with magnesium sulfate anhydride. After the separation of the drying agent, the solvent was distilled away to obtain 15.3 g of the objective product in the form of pale yellow oil.

(3) Synthesis of 1,2,3-trimethyl-4,5,6,7-tetrahydroindene 15.3 g of 1,2,3-trimethyl-4,5,6,7-tetrahydroinde-1-ol as obtained in the foregoing step (2) was diluted with 150 mL of dehydrated ethyl ether, incorporated with several drops of 12 N hydrochloric acid and stirred at room temperature for 2 hours. The resultant mixture was washed with 100 mL of water 3 times and separated into organic phase, which was dried with magnesium sulfate anhydride. After the separation of the drying agent, the solvent was distilled away at atmospheric pressure to obtain 14.05 g of 1,2,3-trimethyl-4,5,6,7-tetrahydroindene.

(4) Synthesis of 1,2,3-trimethyl-4,5,6,7-tetrahydroindenyltrimethylsilane 14.05 g of 1,2,3-trimethyl-4,5,6,7-tetrahydroindene as obtained in the foregoing step (3) was dissolved in 150 mL of dehydrated tetrahydrofuran. To the resultant solution was added dropwise under ice cooling 75 mL of solution of 1.6 M butyllithium in hexane, followed by stirring for 12 hours at room temperature restored. Subsequently the volatile matters in the mixed solution were distilled away at room temperature under reduced pressure, and the resultant solid was washed with hexane to produce white 1,2,3-trimethyl-4,5,6,7-tetrahydroindenyllithium, which was again dissolved in 100 mL of dehydrated tetrahydrofuran. To the resultant solution was added under ice cooling, trimethylchlorosilane which had been subjected to simple distillation, followed by stirring at room temperature for one day and night. Subsequently the volatile matters in the mixed solution were distilled away at room temperature under reduced pressure and the nonvolatile solution was extracted with 300 mL of hexane. The insoluble portion was filtered away and the hexane was distilled away under reduced pressure from the solultion in hexane to recover 18.1 g (77.1 mmol) of 1,2,3-trimethyl-4,5,6,7-tetrahydroindenyltrimethylsilane in the form of pale yellow oil.

(5) Synthesis of 1,2,3-trimethyl-4,5,6,7-tetrahydroindenyltitanium trichloride.

Titanium tetrachloride in an amount of 18.9 g was dissolved in 150 mL of dehydrated toluene. To the resultant solution was added dropwise 18.1 g of 1,2,3-trimethyl-4,5, 6,7-tetrahydroindenyltrimethylsilane which had been obtained in the foregoing step (4) and diluted with 40 mL of dehydrated toluene. Thereafter, the mixed solution was brought into reaction at room temperature for 3 hours, followed by further reaction under refluxing for one hour to obtain dark red solution. Subsequently, the temperature in the reaction system was lowered to 90° C., the insoluble portion was filtered away and the volatile matters in the filtrate were distilled away under reduced pressure to obtain brown solid. The solid was washed with 50 mL of hexane at room temperature, followed by distillation under reduced pressure to recover 1,2,3-trimethyl-4,5,6,7-tetrahydroinden-ltitanium trichloride in the form of dark red solid, which was recrystallized from hexane to obtain 10.5 g (33 mmol) of acicular crystal as the objective product.

The objective product was analyzed by $^1$H-NMR, $^{13}$C-NMR and $^{47}$Ti, $^{49}$Ti-NMR with the results as follows.

$^1$H-NMR (trimethylsilane as standard, heavy chloroform (CDCl$_3$) as solvent):
3.223 to 3.282 ppm (2H, m), 2.573 to 2.647 ppm (2H, m), 2.443 ppm (3H, s), 2.307 ppm (6H, s), 2.009 ppm (2H, m), 1.731 ppm (2H, m)

$^{13}$C-NMR (tetramethylsilane as standard, heavy chloroform (CDCl$_3$) as solvent):
140.00 ppm, 137.73 ppm, 135.03 ppm, 25.63 ppm, 21.87 ppm, 14.52 ppm, 13.72 ppm $^{47}$Ti, $^{49}$Ti-NMR (Chemical shift of $^{47}$Ti in TiCl$_4$ as standard, heavy chloroform (CDCl$_3$) as solvent:
$^{47}$Ti: 347.10 ppm
$^{49}$Ti: 80.730 ppm The schematic synthesis process for Compound A is illustrated as follows:

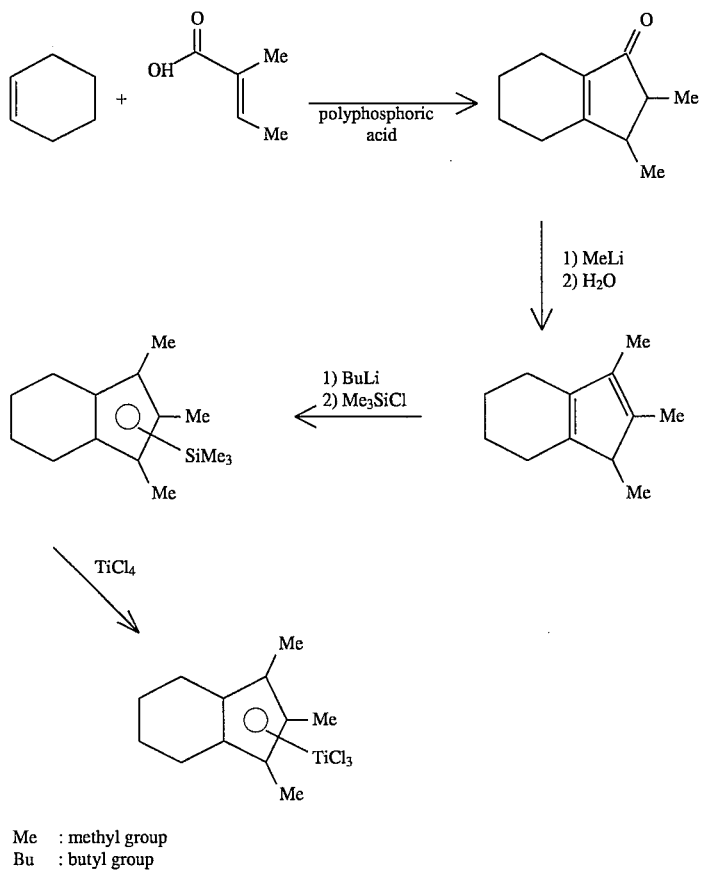

Me : methyl group
Bu : butyl group

EXAMPLE 2

Synthesis of 1,2,3-trimethyl-4,5,6,7-tetrahydroindenyltrimethyltitanium (Compound B)

1.58 g (5.0 mmol) of 1,2,3-trimethyl-4,5,6,7-tetrahydroindenyltitanium trichloride was dissolved in 30 mL of dehydrated tetrahydrofuran, and to the resultant solution was added under ice cooling, 16 mL of solution of 1.0 M methylmagnesium bromide in tetrahydrofuran with stirring for 30 minutes. Subsequently the volatile matters in the mixed solution were distilled away at room temperature under reduced pressure to obtain brown solid, from which soluble matter in 150 mL of hexane was extracted and insoluble matter was filtered away. Thereafter the hexane was distilled away from the filtrate under reduced pressure to obtain 1.32 g of brown oil, which was 1,2,3-trimethyl-4, 5,6,7-tetrahydroindenyltrimethyltitanium and was gradually crystallized at –4° C. The product was analyzed by $^1$H-NMR and $^{13}$C-NMR with the results as follows:

$^1$H-NMR (trimethylsilane as standard, heavy chloroform (CDCl$_3$) as solvent)
2.57 ppm (2H, br), 2.40 ppm (2H, br), 1.99 ppm(3H, s), 1.921 ppm (6H, s), 1.706 ppm(4H, br), 0.832 ppm (9H, s)

$^{13}$C-NMR (tetramethylsilane as standard, heavy chloroform (CDCl$_3$) as solvent)
123.90 ppm, 122.83 ppm, 120.23 ppm, 61.56 ppm, 23.62 ppm, 22.98 ppm, 11.81 ppm, 11.44 ppm

EXAMPLE 3

Synthesis of 1,2,3-trimethyl-4,5,6,7-tetrahydroindenyltitanium trimethoxide (Compound C)

(1) Synthesis of 1,2,3,-trimethyl-4,5,6,7-tetrahydroindenyltrimethylsilane 19.6 g of 1,2,3-trimethyl-4,5,6,7-tetrahydroindene as obtained in Example 1-(3) was dissolved in 70 mL of tetrahydrofuran anhydride. Then the resultant solution was added dropwise at room temperature to 200 mL of suspension of 7.2 g of potassium hydride in tetrahydrofuran anhydride. After the elapse of 1.5 hour, the mixed solution was gradually heated and the reaction was continued under refluxing with heating for 4 hours. When hydrogen was no longer generated, the reaction solution was restored to room temperature, incorporated with 19.6 g of trimethylsilyl chloride and stirred for two days and nights. Subsequently water was added to the reaction liquid to stabilize the excess potassium hydride, then the organic phase was separated, extraction was carried out from the water phase by the use of ethyl ether and the mixture of the extract and the aforesaid organic phase was dried with magnesium sulfate anhydride. Lastly, vacuum distillation was performed to recover 22.7 g of 1,2,3-trimethyl-4,5,6,7-tetrahydroindenyltrimethylsilane.

(2) Synthesis of 1,2,3-trimethyl-4,5,6,7-tetrahydroindenyltitanium trimethoxide

Titanium tetrachloride in an amount of 22.8 g was dissolved in 150 mL of dehydrated toluene. To the resultant solution was added dropwise 22.7 g of 1,2,3-trimethyl-4,5,6,7-tetrahydroindenyltrimethylsilane which had been obtained in the foregoing step (1) and diluted with 70 mL of dehydrated toluene. Thereafter, the mixed solution was brought into reaction at room temperature for 4 hours, followed by further reaction under refluxing for one hour to obtain dark red solution. Subsequently, the temperature in the reaction system was lowered to 90° C., the insoluble portion was filtered away and the filtrate was incorporated, under ice cooling, with 16.2 g of dehydrated methanol and 50.8 g of dehydrated triethylamine, followed by stirring one day and night. Thereafter, the volatile matters in the mixture were distilled away under reduced pressure, the resultant nonvolatile mixture was incorporated with hexane, the insoluble portion was filtered away, the solvent was removed from the filtrate, vacuum distillation was applied to the mixture and the fraction of 128° to 129° C. in boiling point under 1 mm Hg was collected to recover 9.73 g of 1,2,3-trimethyl-4,5,6,7-tetrahydroindenyltitanium trimethoxide in the form of yellow oil. The objective product was analyzed by $^1$H-NMR and $^{13}$C-NMR with the results as follows:

$^1$H-NMR (trimethylsilane as standard, heavy chloroform (CDCl$_3$) as solvent)
  4.07 ppm (9H, s), 2.62 ppm (2H, m), 2.42 ppm (2H, m), 2.04 ppm (3H, s), 2.00 ppm (6H, s), 1.62 ppm to 1.84 ppm (4h, m)

$^{13}$C-NMR (tetramethylsilane as standard, heavy chloroform (CDCl$_3$) as solvent)
  124.52 ppm, 123.44 ppm, 119.38 ppm, 61.40 ppm, 23.00 ppm,
  22.62 ppm, 10.52 ppm, 10.00 ppm

EXAMPLE 4 (polymerization of styrene)

In a 30 mL glass ampule which had been dried and purged with nitrogen were placed 10 mL of styrene, 200 μL of 0.5 mol/L solution of triisobutylaluminum in toluene and 100 μL of 1 mol/L solution of aluminoxane in toluene, followed by sealing the ampule with a teflon cap. Then the ampule was immersed in an oil bath at 70° C. and allowed to stand for 10 minutes. Then, to the resultant mixture was added 50 μL of 10 mmol/L of the Compound A as obtained in Example 1 in toluene to proceed with polymerization at 70° C. for 2 hours. After the completion of the reaction, the content in the ampule was washed with methanol and dried to recover 6.87 g of polymer with a catalytic activity of 287 kg/g-Ti. The polymer was subjected to Soxhlet extraction for 5 hours by the use of boiling methyl ethyl ketone to produce 6.80 g of syndiotactic polystyrene from the insoluble portion. The objective product was a highly stereoregular syndiotactic polystyrene having a weight-average molecular weight of 335,300, a molecular-weight distribution of 2.3, at least 95% syndiotacticity in terms of racemic pentad and a crystal melting point of 270° C.

COMPARATIVE EXAMPLE 1

The procedure in Example 4 was repeated to carry out the polymerization except that 1,2,3-trimethylindenyltitanium trichloride was used in place of the Compound A. As a result, 2.40 g of a syndiotactic polystyrene having a weight-average molecular weight of 250,000 was obtained with a catalytic activity of 100 kg/g-Ti, which was remarkably low as compared with the results in Example 4.

EXAMPLE 5 (polymerization of styrene)

The procedure in Example 4 was repeated to carry out the polymerization except that the polymerization temperature was set on 60° C. As a result, 7.24 g of a syndiotactic polystyrene having a weight-average molecular weight of 426,000 was obtained with a catalytic activity of 302 kg/g-Ti.

EXAMPLE 6 (polymerization of styrene)

The procedure in Example 4 was repeated to carry out the polymerization except that the polymerization temperature was set on 80° C. As a result, 6.18 g of a syndiotactic polystyrene having a weight-average molecular weight of 284.700 was obtained with a catalytic activity of 260 kg/g-Ti.

COMPARATIVE EXAMPLE 2

The procedure in Example 6 was repeated to effect the polymerization except that pentamethylcyclopentadienyltitanium trichloride was used in place of the Compound A. As a result, 4.90 g of a syndiotactic polystyrene having a weight-average molecular weight of 284,000 (almost the same as that in Example 6) was obtained with a catalytic activity of 204 kg/g-Ti, which was considerably low as compared with the results in Example 6.

EXAMPLE 7 (polymerization of styrene)

The procedure in Example 5 was repeated to perform the polymerization except that the Compound C as obtained in Example 3 was used in place of the Compound A. The resultant polymer in an amount of 6.95 g was subjected to Soxhlet Extraction for 5 hours by the use of boiling methyl ethyl ketone to produce 686 g of syndiotactic polystyrene from the insoluble portion with a catalytic activity of 286 kg/g-Ti. It had a weight-average molecular weight of 453,000.

EXAMPLE 8 (polymerization of styrene)

N,N-dimethylaniliniumtetrakis(pentafluorophenyl)borate in an amount of 0.064 g was suspended in 31.6 mL of toluene, and the resultant suspension was incorporated with 0.4 mL of 2.0 mol/L solution of triisobutylaluminum in toluene and then with 8 mL of 10 mmol/L solution of the Compound B as obtained in Example 2 in toluene to prepare a catalyst solution.

Subsequently, in a glass ampule were placed 10 mL of styrene and 20 μL of 0.5 mol/L solution of triisobutylaluminum in toluene, followed by sealing the ampule with a teflon cap. The content in the ampule was heated to 70° C. and incorporated with 188 μL of the above-prepared catalyst solution to proceed with polymerization at 70° C. for 4 hours. After the completion of the reaction, the content was washed with methanol and dried to recover 5.17 g of polymer with a catalytic activity of 288 kg/g-Ti. The polymer was subjected to Soxhlet extraction for 5 hours by the use of boiling methyl ethyl ketone to produce 5.08 g of syndiotactic polystyrene from the insoluble portion. The objective syndiotactic polystyrene had a weight-average molecular weight of 906,000.

What is claimed is:

1. A polymerization catalyst for a compound containing an ethylenically unsaturated double bond or an acetylenic bond, which catalyst comprises:

(A) a transition metal compound represented by formula (I)

$$RMX_{a-1}L_b \qquad (I)$$

wherein R is, as a π ligand, a fused bicyclic or tricyclic cyclopentadienyl group in which at least one of many-membered rings to which a cyclopentadienyl group is fusedly bonded is a saturated ring; M is a transition metal, X is a σ ligand, a plurality of moieties X may be the same or different, L is a Lewis base, a is the valency of moiety M, b is 0, 1 or 2 and when L is a plurality, each L may be the same or different; and (B) an aluminoxane.

2. A polymerization catalyst for a compound containing an ethylenically unsaturated double bond or an acetylenic bond, which catalyst comprises:

(A) a transition metal compound represented by formula (I)

$$RMX_{a-1}L_b \qquad (I)$$

wherein R is, as a π ligand, a fused bicyclic or tricyclic cyclopentadienyl group in which at least one of many-membered rings to which a cyclopentadienyl group is fusedly bonded is a saturated ring; M is a transition metal, X is a σ g ligand, a plurality of moieties X may be the same or different, L is a Lewis base, a is the valency of moiety M, b is 0, 1 or 2 and when L is a plurality, each L may be the same or different;

component (B) is at least one member selected from the group consisting of an (1) aluminoxane, (2) an ionic compound comprising a noncoordinating anion and a cation, and (3) an organoboron compound; and (C) a Lewis acid.

3. A polymerization catalyst for a compound containing an ethylenically unsaturated double bond or an acetylenic bond, which catalyst comprises:

(A) a transition metal compound represented by formula (I)

$$RMX_{a-1}L_b \qquad (I)$$

wherein R is, as a π ligand, a fused bicyclic or tricyclic cyclopentadienyl group in which at least one of many-membered rings to which a cyclopentadienyl group is fusedly bonded is a saturated ring; M is a transition metal, X is a σ ligand, a plurality of moieties X may be the same or different, L is a Lewis base, a is the valency of moiety M, b is 0, 1 or 2 and when moiety L is a plurality, each L may be the same or different; and component (B) is an ionic compound comprising a noncoordinating anion and a cation; and component (C) is a Lewis acid.

4. The transition metal compound according to claim 1, wherein R is selected from the fused polycyclic cyclopentadienyl group represented by any one of formulae (II) to (IV)

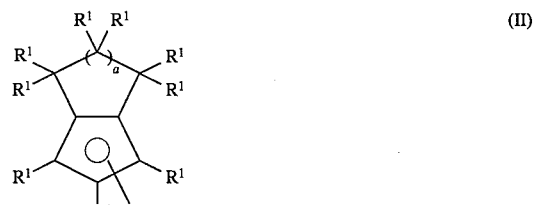

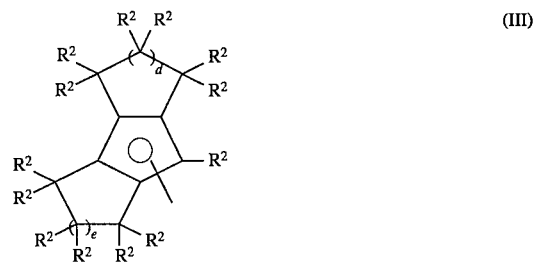

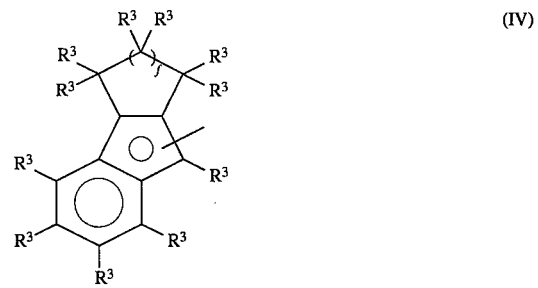

wherein $R^1$, $R^2$ and $R^3$ are each hydrogen, halogen, an aliphatic hydrocarbon group having 2 to 20 carbon atoms, an aromatic hydrocarbon group having 6 to 20 carbon atoms, an alkoxy group having 1 to 20 carbon atoms, an aryloxyl group having 6 to 20 carbon atoms, a thioalkoxy group having 1 to 20 carbon atoms, a thioaryloxyl group having 6 to 20 carbon atoms, an amino group, an amide group, a carboxyl group or an alkylsilyl group and may be the same as or different from each other; and c, d, e and f are each an integer of one or greater.

5. The transition metal compound according to claim 2, wherein R is selected from the fused polycyclic cyclopentadienyl group represented by any one of formulae (II) to (IV)

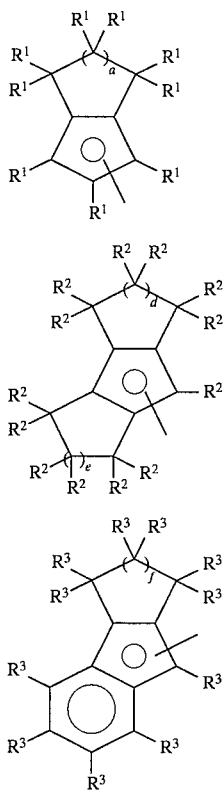

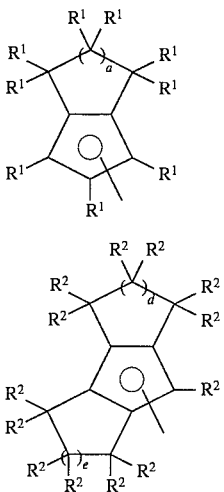

wherein $R^1$, $R^2$ and $R^3$ are each hydrogen, halogen, an aliphatic hydrocarbon group having 2 to 20 carbon atoms, an aromatic hydrocarbon group having 6 to 20 carbon atoms, an alkoxy group having 1 to 20 carbon atoms, an aryloxyl group having 6 to 20 carbon atoms, a thioalkoxyl group having 1 to 20 carbon atoms, a thioaryloxyl group having 6 to 20 carbon atoms, an amino group, an amide group, a carboxyl group or an alkylsilyl group and may be the same as or different from each other; and c, d, e and f are each an integer of one or greater.

6. The transition metal compound according to claim 3, wherein R is selected from the fused polycyclic cyclopentadienyl group represented by any one of formulae (II) to (IV)

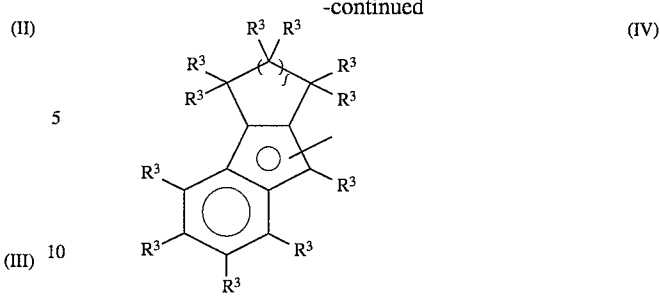

wherein $R^1$, $R^2$ and $R^1$ are each hydrogen, halogen, an aliphatic hydrocarbon group having 2 to 20 carbon atoms, an aromatic hydrocarbon group having 6 to 20 carbon atoms, an alkoxy group having 1 to 20 carbon atoms, an aryloxyl group having 6 to 20 carbon atoms, a thioalkoxyl group having 1 to 20 carbon atoms, a thioaryloxyl group having 6 to 20 carbon atoms, an amino group, an amide group, a carboxyl group or an alkylsilyl group and may be the same as or different from each other; and c, d, e and f are each an integer of one or greater.

7. The polymerization catalyst of claim 4, wherein R is a 4,5,6,7-tetrahydroindenyl group.

8. The polymerization catalyst of claim 5, wherein R is a 4,5,6,7-tetrahydroindenyl group.

9. The polymerization catalyst of claim 6, wherein R is a 4,5,6,7-tetrahydroindenyl group.

10. A process for producing a polymer of a compound containing an ethylenically unsaturated double bond or a polymer of an acetylenic compound, which comprises:

polymerizing said ethylenically unsaturated compound or said acetylenic compound in the presence of the polymerization catalyst of claim 1.

11. A process for producing a polymer of a compound containing an ethylenically unsaturated double bond or a polymer of an acetylenic compound, which comprises:

polymerizing said ethylenically unsaturated compound or said acetylenic compound in the presence of the polymerization catalyst of claim 2.

12. A process for producing a polymer of a compound containing an ethylenically unsaturated double bond or a polymer of an acetylenic compound, which comprises:

polymerizing said ethylenically unsaturated compound or said acetylenic compound in the presence of the polymerization catalyst of claim 3.

13. A process for producing a styrenic polymer, which comprises:

copolymerizing a styrenic monomer and another polymerizable unsaturated compound in the presence of the polymerization catalyst of claim 1.

14. A process for producing a styrenic polymer, which comprises:

copolymerizing a styrenic monomer and another polymerizable unsaturated compound in the presence of the polymerization catalyst of claim 2.

15. A process for producing a styrenic polymer, which comprises:

copolymerizing a styrenic monomer and another polymerizable unsaturated compound in the presence of the polymerization catalyst of claim 3.

16. The process of claim 13, wherein said styrenic polymer exhibits a high degree of syndiotacticity.

17. The process of claim 14, wherein said styrenic polymer exhibits a high degree of syndiotacticity.

18. The process of claim 15, wherein said styrenic polymer exhibits a high degree of syndiotacticity.

* * * * *